United States Patent
Lukas

(10) Patent No.: US 11,885,668 B2
(45) Date of Patent: Jan. 30, 2024

(54) SENSOR ASSEMBLY, FURNITURE AND METHOD FOR DETECTING ACTIVITY OF A USER OF A FURNITURE

(71) Applicant: LOGICDATA Electronic & Software Entwicklungs GmbH, Deutschlandsberg (AT)

(72) Inventor: Stefan Lukas, Preding (AT)

(73) Assignee: LOGICDATA Electronic & Software Entwicklungs GmbH, Deutschlandsberg (AT)

( * ) Notice: Subject to any disclaimer, the term of this patent is extended or adjusted under 35 U.S.C. 154(b) by 961 days.

(21) Appl. No.: 16/848,762

(22) Filed: Apr. 14, 2020

(65) Prior Publication Data

US 2020/0326227 A1    Oct. 15, 2020

(30) Foreign Application Priority Data

Apr. 15, 2019    (DE) .......................... 102019109889.0

(51) Int. Cl.
*G01H 9/00*    (2006.01)
*G01V 8/12*    (2006.01)
(Continued)

(52) U.S. Cl.
CPC ............ *G01H 9/00* (2013.01); *A61B 5/0205* (2013.01); *A61B 5/6891* (2013.01); *G01V 8/12* (2013.01);
(Continued)

(58) Field of Classification Search
CPC ...... G01H 9/00; A61B 5/0205; A61B 5/6891; A61B 5/02416; A61B 5/08; A61B 5/1118;
(Continued)

(56) References Cited

U.S. PATENT DOCUMENTS

| 4,247,847 A | 1/1981 | Gontowski, Jr. |
| 4,763,740 A * | 8/1988 | Pattern ..................... G01G 9/00 177/229 |

(Continued)

FOREIGN PATENT DOCUMENTS

| CN | 1924536 A * | 3/2007 | ............... G01H 9/00 |
| DE | 10261345 A1 | 7/2004 | |

(Continued)

*Primary Examiner* — Ryan D Walsh
(74) *Attorney, Agent, or Firm* — Morgan, Lewis & Bockius LLP

(57) ABSTRACT

A sensor assembly for a furniture for detecting an activity of a user of the furniture comprises a light transmitter and a light receiver forming beginning and end of an optical light path connecting the light transmitter and the light receiver. The light receiver is configured to output a reception signal based on a received amount of light. The sensor assembly further comprises an evaluation circuit which is configured to generate a movement signal based on the reception signal or a signal derived from the reception signal, and an oscillating body which is movably mounted in such a way that a movement of the oscillating body results in a change in a property of the light path. The sensor assembly is arranged such that the activity of the user causes the oscillating body to oscillate.

25 Claims, 8 Drawing Sheets

(51) Int. Cl.
  *A61B 5/0205* (2006.01)
  *A61B 5/11* (2006.01)
  *A61B 5/08* (2006.01)
  *A61B 5/00* (2006.01)
  *A61B 5/024* (2006.01)

(52) U.S. Cl.
  CPC ....... *A61B 5/02416* (2013.01); *A61B 5/02438* (2013.01); *A61B 5/08* (2013.01); *A61B 5/1118* (2013.01); *A61B 5/4815* (2013.01)

(58) Field of Classification Search
  CPC .......... A61B 5/4815; A61B 2562/0233; G01V 8/12; A47B 2220/0091
  See application file for complete search history.

(56) References Cited

U.S. PATENT DOCUMENTS

| | | | | |
|---|---|---|---|---|
| 9,326,597 B2 * | 5/2016 | Lukas | ...................... | A47B 9/00 |
| 9,592,006 B2 | 3/2017 | Oakhill | | |
| 11,662,200 B2 * | 5/2023 | Krasser | .................. | G01B 11/16 |
| | | | | 356/32 |
| 2005/0011738 A1 * | 1/2005 | Smith | .................... | A61B 5/1113 |
| | | | | 200/85 R |
| 2009/0016735 A1 * | 1/2009 | Schmitz | .................. | G01V 8/12 |
| | | | | 398/140 |

FOREIGN PATENT DOCUMENTS

| | | | | |
|---|---|---|---|---|
| DE | 102009043535 A1 * | 3/2011 | ............. | A61B 5/103 |
| DE | 102015217200 A1 * | 3/2017 | ............. | B23Q 17/12 |
| DE | 202016105633 U1 | 3/2017 | | |
| DE | 202016105634 U1 | 3/2017 | | |
| DE | 202016105635 U1 | 3/2017 | | |
| DE | 202016103605 U1 | 4/2017 | | |
| DE | 202017102920 U1 | 8/2018 | | |
| DE | 102018109215 A1 | 10/2019 | | |
| WO | WO-2013027145 A2 * | 2/2013 | ........... | A61B 5/1038 |
| WO | WO-2013/132378 A1 | 9/2013 | | |
| WO | WO-2018/210856 A1 | 11/2018 | | |
| WO | WO-2019/201799 A1 | 10/2019 | | |

* cited by examiner

SENSOR ASSEMBLY, FURNITURE AND METHOD FOR DETECTING ACTIVITY OF A USER OF A FURNITURE

BACKGROUND OF THE INVENTION

The present disclosure relates to a sensor assembly for a furniture for detecting an activity of a user, to a furniture comprising such a sensor assembly, and to a method for detecting an activity of a user of a furniture.

Sensors for monitoring activities, such as physiological parameters of a person, are known especially in the field of fitness and activity trackers. Here, for example, the heartbeat or respiration are measured and evaluated periodically or continuously, so that the user gets an overview of, for example, his or her sporting and physical condition.

However, recent studies show that the quality of sleep can also have a significant impact on a person's performance during the day. In particular, the quality of sleep also affects the "fitness" of people at the workplace, which is why suitable solutions are not only of interest to private individuals but also to companies that care about the fitness of their employees at work.

Conventional solutions for monitoring daily activities, such as fitness wristbands, are sometimes suitable for measuring physiological parameters during the night, but they are typically discarded by the user during the night for comfort and/or charging with a charger. In addition, a considerable number of people find wearing a fitness tracker generally disturbing and uncomfortable. Another disadvantage of conventional fitness trackers is the specialization on a few specific parameters, such as the user's pulse, while other parameters, such as sounds and movements, which can also be important for the evaluation of sleep quality, are ignored due to the lack of suitable sensors.

Conventional solutions for the measurement of nocturnal activities in particular are based on the measurement of force or pressure changes. The force exerted by a person lying in bed on the mattress and on a sensor that is placed on or under the mattress is measured. A movement leads to a change in force or pressure, which can be detected in the measured signal. The heartbeat or breathing of a user can be determined by periodic changes in force or pressure.

The problem with these solutions, however, is that a sensor for a bed that is placed on the mattress can slip or affect the user's sleeping comfort. If the sensor s placed under the mattress, the sleeping comfort is not affected, but the already small changes in force are strongly damped, so that they are difficult or even impossible to measure. A further complicating factor is that at this position, vibrations from the bed's surroundings can also be coupled in via the bed frame and must be filtered or damped electronically or mechanically accordingly. The installation of sensors inside the mattress is a compromise, but does not allow the retrofitting of existing mattresses.

SUMMARY OF THE INVENTION

This disclosure provides an improved concept for the measurement of nocturnal activities of a user.

The improved concept is based on the idea of providing highly sensitive sensors for measuring activities, such as physiological parameters, and placing them close to a furniture or on the furniture itself in such a way that the comfort of the user is not impaired. For this purpose a sensor with a movable element is used, which is set into a mechanical oscillation by movements of the user of the furniture. The oscillation is detected and evaluated by optical means. Oscillation frequencies and/or amplitudes determined in this way allow conclusions to be drawn about periodically recurring vibrations, for example, triggered by physiological parameters such as the user's heartbeat or breathing, as well as other movements or sound.

For example, a sensor assembly for a furniture for detecting an activity of a user of the furniture according to the improved concept comprises a light transmitter and a light receiver, which form the beginning and end of an optical light path and are connected to each other via this light path. The light receiver is configured to emit a reception signal based on a received amount of light. The sensor assembly also has an oscillating body which is movably mounted in such a way that movement of the oscillating body results in a change in a property of the light path. Furthermore, an evaluation circuit of the sensor assembly is configured to generate a motion signal based on the reception signal or a signal derived from the reception signal. The sensor assembly is configured to be mounted in or on a furniture in such a way that the activity of the user of the furniture causes the oscillating body to oscillate.

The light transmitter is a light-emitting element, such as a light-emitting diode (LED) or a laser diode. The light receiver is an element, such as a photodiode, which converts light incident on the light receiver into an electrical reception signal proportional to the amount of light received. The light transmitter and the light receiver are aligned with each other in such a way that at least a part of the emitted light of the light transmitter strikes a photosensitive part of the light receiver if the oscillating body does not block the light completely. In other words, the light transmitter and the light receiver are connected by a light path. The light path has properties such as length and orientation as well as optical properties such as absorption, reflection or scattering.

The oscillating body is, for example, a flexible tab that influences the amount of light in the light path. The amount of light is influenced by the flexible tab, for example by absorption, reflection or scattering. Without oscillation of the flexible tab, the light receiver receives a defined constant amount of light. This amount of light can be called the standard amount of light. A change in position of the flexible tab relative to the light path changes the amount of light received at the light receiver at constant output power or constant emitted amount of light of the light transmitter. Consequently, an oscillation of the oscillating body causes a periodically changing amount of light received by the light receiver. The oscillating body is attached to the furniture in such a way that an oscillation is stimulated by the corresponding activity of the user. For example, in a bed, vibrations triggered by the movement or a physiological parameter, e.g. the heartbeat, of a user lying in bed are transmitted via the mattress and possibly the bed frame to the oscillating body of the sensor assembly. Furthermore, in the case of a table or a piece of seating furniture, the presence of the user can be determined by movement or oscillation of the oscillating body, for example triggered by physiological parameters of the user.

The evaluation circuit is configured to generate a motion signal based on the reception signal. For example, the motion signal corresponds to a detected periodicity of the reception signal, in particular e.g. amplitude and/or frequency of at least one oscillation mode of the oscillating body. This movement signal can then be evaluated, for example, in such a way that a user receives information about the desired activity or the desired physiological parameters.

In some embodiments, the oscillation influences the amount of light received by the light receiver from the light transmitter. An oscillation of the oscillating body causes e.g. a periodically changing absorption, reflection or scattering of the light on the light path. For example, this change causes the amount of light received at the light receiver oscillating periodically between a maximum and a minimum amount of light around a standard amount of light.

In some embodiments, the evaluation circuit is further configured to control an amount of light emitted by the light transmitter by means of a control signal resulting from minimizing a difference between the reception signal and a reference signal. Furthermore, the evaluation circuit in these embodiments can be configured to generate the motion signal based on the control signal or on a signal derived from the control signal.

In addition to measuring the amount of light received, a control system can be provided which keeps the amount of light received at the light receiver constant by varying the amount of light emitted by the light transmitter. A control variable for the light transmitter can then serve as the basis for a measure of the movement or oscillation of the oscillating body, for example as a movement signal. As mentioned above, the difference or variation in the amount of light received is compensated for by adjusting the amount of light emitted by the light transmitter accordingly. If, for example, the movement of the oscillating body leads to a reduction in the amount of light received, the amount of light emitted is increased until the amount of light received corresponds again to the amount of light without movement of the oscillating body, i.e. the standard amount of light. If the oscillation leads to an increase in the amount of light received, then correspondingly less light is emitted.

In some embodiments, the evaluation circuit comprises a filter stage and is configured to generate the motion signal by filtering the reception signal or the signal derived from the reception signal with the filter stage.

The filter stage can be a low-pass filter stage with a differentiator downstream of the low-pass filter stage. Alternatively, the filter stage can be a bandpass filter stage. The use of a bandpass filter, for example, has the effect of filtering out high-frequency interfering signals as well as low-frequency slow signal changes that have nothing to do with the user's activity. Since a differentiator also has a high-pass effect, the combination of a low-pass filter and the differentiator ultimately results in the transfer behavior of a bandpass.

In addition to filtering or integrated into filtering, amplification, in particular adaptive gain control, can also be provided, for example to increase the signal range.

In some embodiments, the activity is a biological activity and includes at least one of the following: heartbeat, pulse, movement, sound, and breathing. The physiological parameters mentioned above are particularly suitable for a precise assessment of sleep quality. While heartbeat and pulse are often used by conventional fitness trackers to evaluate sleep quality, the user's own movement, breathing and sound are also important measurements that characterize sleep quality. While fitness trackers and force or pressure sensors are not designed for such measurements, the oscillating body of the sensor assembly can also be linked to these types of activity, allowing a complete and accurate analysis of sleep quality.

In some embodiments, the oscillating body is mounted flexibly such that the oscillating body has only one mechanical degree of freedom. It has been shown that certain physiological parameters of a person lying in bed, such as the heartbeat, generate significantly stronger vibrations in the horizontal direction along the length of the person compared to vibrations in the vertical direction, i.e. towards a force or pressure sensor of conventional solutions, for example, which is positioned underneath the lying person or under a mattress of the bed. This is because the heart pumps blood through the veins, which mainly extend along the head-foot axis, and in a lying person this creates "shock waves" in a horizontal direction.

It is therefore advantageous to mount the sensor on or in the bed frame or on a mattress in such a way that the oscillating body only oscillates in exactly one direction, namely in the direction of the blood flow of a lying person. Vibrations in other directions, on the other hand, can be damped or completely prevented by a shape or alignment of the oscillating body. This effectively suppresses or decouples vibrations not caused by the heartbeat, for example by massage actuators of the bed or external influences.

For an arrangement in a seating surface of a piece of seating furniture, such as an office chair or armchair, the direction of vibration would also be parallel to the seating surface, i.e. horizontal to the floor on which the piece of seating furniture is standing. In the case of an arrangement in a backrest, however, the direction of the blood flow has no influence. Here, a vertical direction of oscillation would be preferred. The use of the sensor assembly in both seating furniture and tables enables the presence of the user to be detected by the movement of the oscillating body triggered by simple shocks or by a combination of shocks and physiological activities. For tables, e.g. electrically adjustable tables, the sensor assembly can be integrated into the table frame, for example.

In some embodiments, the oscillating body has a resonance frequency lower than 20 Hz, in particular in the range of 12-14 Hz, Measurement experiments have shown that, especially for measurements of physiological vibrations, the oscillating body ideally has a resonance frequency of about 13 Hz. This can be achieved by selecting the shape and material or the material thickness of the oscillating body.

In some embodiments, the light path is designed as a direct optical connection for transmitting light from the light transmitter to the light receiver. Optionally, the transmission takes place without the use of reflections. In particular, light transmission is not based on the reflection of light rays from a surface. Similarly, the transmission is not based on the deformation of an optical fiber and an evaluation of a related change in the amount of light.

An advantage of the improved concept is that the measuring principle is not based on a reflection measurement of a surface, but on oscillations of a component of the sensor itself, which are caused by an activity of the user. This means that existing furniture systems can be easily retrofitted without the need for specially adapted mattresses or other elements.

In some embodiments, the light path is shorter than 1 cm, in particular shorter than 5 mm. For example, a diameter or width of the light path is smaller than 1 mm, in particular smaller than 500 µm, and is about 200 µm, for example. A cross sectional area of the light path is thus smaller than 1 $mm^2$, in particular smaller than 0.25 $mm^2$ and is, for example, in the range of about 0.04 $mm^2$. For example, the light transmitter is an LED or a laser diode in the infrared range.

In some embodiments, the light transmitter or the light receiver is attached to the oscillating body. This allows a relative movement between light transmitter and light receiver, so that an oscillation causes the alignment of light receiver and light transmitter to vary and thus influences the amount of light received at the light receiver. In other words, the orientation and/or the length of the light path is changed by the vibration in such designs.

In some embodiments, the oscillating body is arranged between the light transmitter and the light receiver in such a way that a translucent part of the oscillating body is located on the light path, the movement of the oscillating body causing a change in an optical property of the light path within the translucent part.

For example, the translucent part is characterized by a transmission that depends on a position and/or a direction of extension of the optical path of light within the translucent part. For example, the dependency is a consequence of a structure of the translucent part, which leads to varying absorption, reflection or scattering within or on a surface of the translucent part. For example, a surface of the translucent part has a significant roughness. Alternatively, the translucent part has a varying thickness and/or optical density. For example, the translucent part is made of a silicate such as glass or a plastic.

In some embodiments, the oscillating body comprises an aperture element which is configured to cover the light path at least partially, wherein the movement of the oscillating body causes a change in the coverage of the light path.

The aperture element of the oscillating body can move into the light path to influence the amount of light received by the light receiver. During operation of the sensor, the aperture element is set in motion by the oscillation, for example triggered by an activity of the user, in such a way that an oscillation of the oscillating body leads to an oscillation of the aperture element relative to the light path and thus to an influence on the amount of light received.

The shape of the aperture element can be selected in different ways. For example, the aperture element has the shape of a cone, a truncated cone, a pyramid, a truncated pyramid, a cylinder, a parallelepiped, a truncated cone or a shape composed of several of those shapes.

The choice of the shape of the diaphragm element also results in a cross-sectional area perpendicular to the light path, with which the diaphragm element penetrates the light path. The light path forms the normal to this cross-sectional area, so to speak. For example, the cross-sectional area is at least partially formed by at least one of the following shapes: Rectangle, triangle, trapezium, circle segment, ellipse segment. For example, the cross-sectional area is formed by combining a rectangle with a triangular or trapezoidal shape or a semicircular shape, without excluding other possible combinations.

Cross-sectional areas with a width varying along the deflection of the oscillation can cause a more continuous course of the amount of light change. In particular, when the aperture element penetrates the light path, i.e. when it passes from no cover to a partial cover, it may be advantageous if the corresponding end of the diaphragm element is less wide than the light path to allow a continuous transition.

In some embodiments, the position or mounting of the aperture element in relation to the light path is selected so that in the resting state or without oscillation, the amount of light emitted is greater by a defined factor than the amount of light received, for example twice as much. This can be achieved, for example, by a defined coverage of the light path by the diaphragm element in the resting state, for example by approximately 50% coverage, particularly in the range between 40% and 60%. This allows deflections of the oscillating body in both directions along the direction of movement of the aperture element to be detected.

In some embodiments, the sensor assembly further comprises a printed circuit board on which at least part of the evaluation circuit is located. For example, light transmitter and light receiver are arranged on a common printed circuit board. Alternatively, a part, for example the light transmitter or the light receiver is arranged on a tab which is fixed to the printed circuit board. Optionally, the light path is parallel or essentially parallel to the main plane or surface of the printed circuit board. In particular, an angle between the light path and the surface of the printed circuit board is smaller than 10°, in particular smaller than 5°. The circuit board may also include electronics for motor control and/or actuator control of an adjustable furniture.

The deflection of the oscillating body is optionally perpendicular to the light path or perpendicular or parallel to the surface or main plane of the printed circuit board. Small angular deviations, as just mentioned, can be tolerated. For example, the oscillating body is a part of the circuit board, i.e. the circuit board includes a springy or flexible part, such as a flexible L-shaped or meandering tab.

In some embodiments, the light transmitter or the light receiver is attached to the oscillating body, so that an oscillation results in a relative movement between the light transmitter and the light receiver. For example, one end of the light path, e.g. the light transmitter, is located on a first part of the circuit board, which is rigidly fixed opposite the oscillating body. The other end of the light path, e.g. the light receiver, is located on a second part of the circuit board opposite the light transmitter, the second part representing the oscillating body and allowing a relative movement to the first part of the circuit board. Alternatively, the circuit board has two oscillating bodies, for example two flexible tabs, whereby the light receiver and the light transmitter are each attached to one of the two flexible tabs.

In some embodiments, the printed circuit board has an opening below the light path, with the oscillating body being arranged movably above and/or in the opening.

In some embodiments, the sensor assembly further comprises a housing, in particular a light-protected housing, in which the light transmitter, the light receiver and the oscillating body are arranged. The sensor assembly is optionally arranged in a housing. The housing does not have to be completely closed, but the housing ensures that the light receiver is not exposed to ambient light, but only receives light from the light transmitter. This prevents the measurement of the received light power from the light transmitter from being impaired or falsified.

In some embodiments, the sensor assembly further comprises additional light transmitters and/or light receivers, each light receiver being connected to at least one light transmitter via an optical light path.

For example, the light path connects several transmitters and/or several receivers. Alternatively, the additional light transmitters and/or light receivers form a combination of several light paths offset to each other (e.g. 90°). For example, the light paths are perpendicular to each other. In such a configuration, a direction of the user's activity can be determined more precisely.

The improved measurement concept is also implemented by a furniture with at least one sensor assembly according to one of the previously described embodiments. This includes the possibility of integrating the sensor assembly into an actuator and/or into a control system of the furniture, which for example has at least one electrically adjustable component. The sensor assembly is attached to the furniture frame in such a way that the light transmitter, the light receiver and the oscillating body are isolated from ambient light. For example, the sensor assembly is located in a cavity, especially in a light-protected cavity of the furniture frame.

The furniture is for example a bed, a seat or a table. The sensor assembly is aligned with the furniture in such a way that the user of the furniture is active in a direction that corresponds to a deflection of the oscillating body of the sensor assembly. For example, the furniture is a bed and the oscillating body of the sensor assembly is aligned so that a deflection of the vibration is parallel to the longitudinal direction of the bed. This ensures that a heartbeat of a lying user can be measured and thus generate an oscillation of the oscillating body. It is known that the heartbeat generates shock waves in a horizontal direction that extend along the length of the user. In other words, the heartbeat generates shock waves that propagate primarily from the user's heart to his head or feet.

Further embodiments of the furniture result directly from combinations of the embodiments of the sensor assembly described above.

The improved measurement concept is also implemented by a method for detecting the activity of a user of a furniture. Such a furniture is equipped with at least one sensor assembly. The at least one sensor assembly comprises a light transmitter and a light receiver, which are connected to each other via an optical light path, and an oscillating body. The oscillating body is arranged movably in such a way that a movement of the oscillating body results in a change of a property of the light path.

According to the method, a first amount of light is emitted from the light transmitter via the light path to the light receiver. The light receiver generates a reception signal based on a second amount of light received via the light path. An activity of the user, such as breathing or heartbeat, is converted into a change in the movement of the oscillating body relative to the light path. A motion signal is generated based on at least the second amount of light or on a signal derived from the second amount of light. Based on the motion signal, especially based on a change in the motion signal, the activity of the user is detected.

Further developments of the method result directly from the different embodiments of the sensor assembly, the actuator, the control system and the furniture, which have been described in detail above. This concerns in particular the generation, processing and evaluation of the various signals used.

BRIEF DESCRIPTION OF THE DRAWINGS

In the following, the invention is explained in detail by means of exemplary embodiments with reference to the drawings. Components that are functionally identical or have an identical effect may be provided with identical reference symbols. Identical parts or parts with identical function may be explained only in terms of the figure in which they first appear. The explanation is not necessarily repeated in the following figures.
In the Drawings.

DETAILED DESCRIPTION

Figure 1:
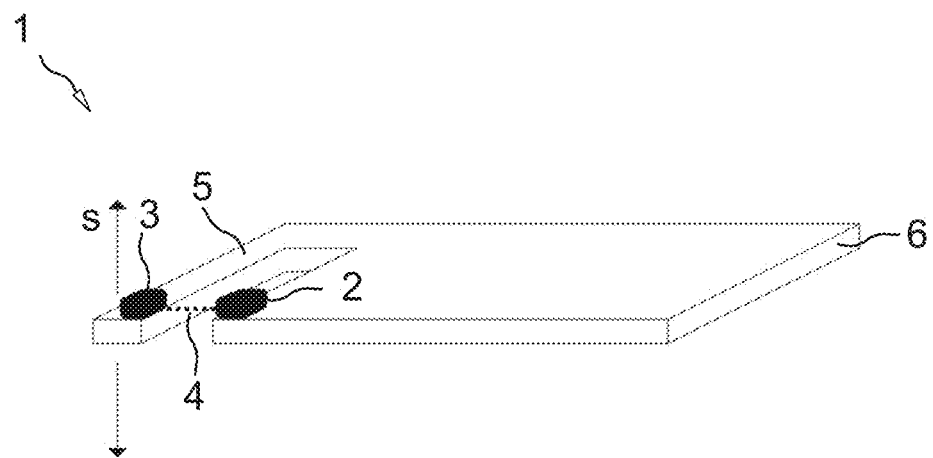
FIGS. 1 to 7 show different embodiments of a sensor assembly according to the improved concept.

FIG. 1 shows an exemplary embodiment of a sensor assembly 1, which comprises a printed circuit hoard 6, on which a light transmitter 2 and a light receiver 3 are arranged, which are optically connected to each other via a light path 4. The light transmitter 2 and the light receiver 3 can also be arranged in a sensor assembly 1 out printed circuit hoard 6. In this embodiment, the light receiver 3 is mounted on a second part of the circuit board 6 and is designed as an oscillating body 5. The oscillating body 5, for example, is designed as a flexible tab. This tab formed by a recess in the printed circuit board 6. As an alternative to the structure shown, the positions of light transmitter 2 and light receiver 3 can also be reversed. The light path 4 in a rest position or at zero deflection of the oscillator 5 corresponds to the direction of the emitted light from the light transmitter 2 and is parallel to the surface of the printed circuit board 6.

The oscillating body 5 has a mechanical degree of freedom s, along which a movement or oscillation can occur as a deflection of the oscillating body 5. In this embodiment, the mechanical degree of freedom s is the only mechanical degree of freedom that can be excited to oscillate and is oriented perpendicular to the light path 4 but parallel to the normal of the surface of the printed circuit board 6. The printed circuit board 6 is designed to be firmly connected to a furniture so that the light receiver is rigidly fixed on a first part of the printed circuit board 6 opposite the oscillating body and opposite the furniture. Furthermore, the printed circuit board 6 is connected to the furniture in such a way that the oscillating body 5 can deflect or oscillate along the degree of freedom s, so that a relative movement between light transmitter 2 and light receiver 3 is possible.

The Light transmitter 2 emits a first amount of light. Without oscillation of the oscillating body 5, the light receiver 3 receives a defined constant second amount of light, which corresponds, for example, to the first amount of light and can be called the standard amount of light. The light transmitter 2 and the light receiver 3, for example, operate in the infrared light range. A change in the position of the oscillating body 5 results in an alignment between the light transmitter 2 and the light receiver 3 being varied. In other words, an alignment of the light path 4 varies from the direction of the emitted light from the light transmitter 2, resulting in a periodically changing second amount of light received by the light receiver 3. For example, the second amount of light oscillates in the range between no received light and the first amount of light. Based on the embodiment shown in FIG. 1, where the maximum amount of light is at zero deflection of the oscillating body 5, one frequency of the oscillating second amount of light corresponds to twice the frequency of the oscillation of the oscillating body 5. Alternatively, however, the embodiment can be adapted, for example, so that the frequencies mentioned are the same.

The light transmission via the light path 4 from the light transmitter 2 to the light receiver 3 is based on a direct optical transmission and is in particular not dependent on reflectors or the like which catch stray light from the light path 4 or otherwise guide light from the light transmitter 2 to the light receiver 3. The use of one or more optical fibers is also avoided.

An evaluation circuit of the sensor assembly 1, which is not shown in FIG. 1 for the sake of clarity, determines the frequency of the oscillation of the oscillating body 5 from the reception signal of the light receiver 3 and generates a motion signal which contains, for example, information about the amplitude and frequency of the oscillation of the oscillating body 5.

Figure 2:
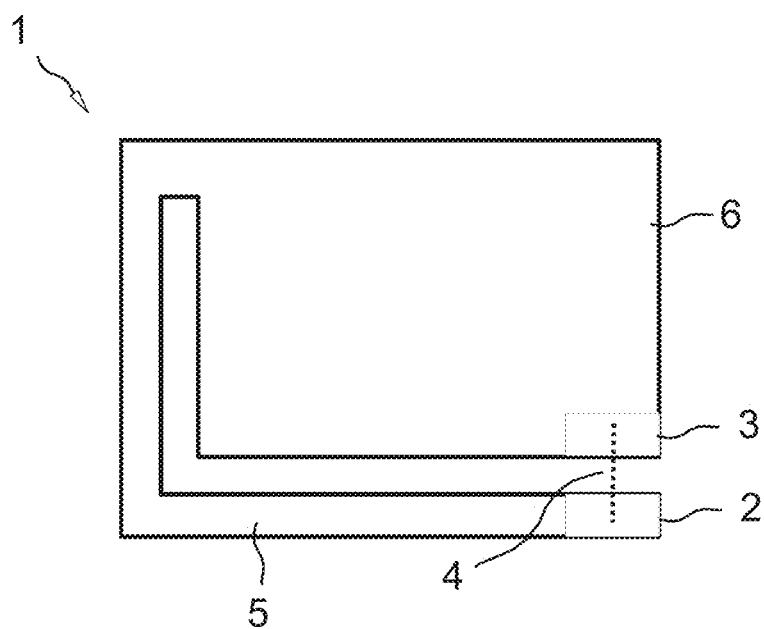

FIG. 2 shows a top view of another embodiment of a sensor assembly 1 similar to the one of FIG. 1. The difference to the embodiment of FIG. 1 is the shape of the recess, which here defines an L-shaped flexible tab as oscillating body 5. To increase the mechanical response, the effective mass of the oscillating body 5 can be increased by extending the recess in this way. Furthermore, this can also lead to a higher amplitude of the vibration of the oscillating body 5, which in turn can enable a more sensitive measurement of the oscillation.

Figure 3:
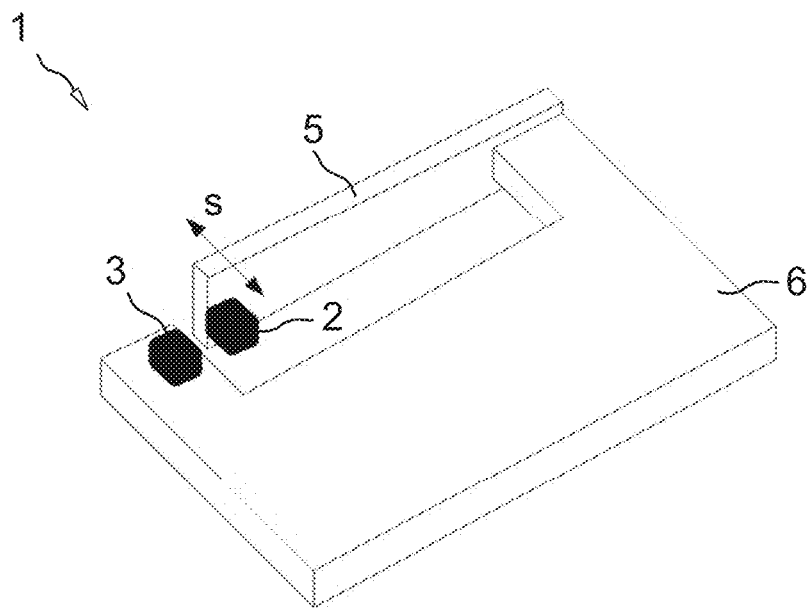

FIG. 3 shows a further embodiment of a sensor assembly 1 based on the embodiment of FIG. 1, in which the oscillating body 5 is designed in such a way that its mechanical degree of freedom s is both perpendicular to the light path 4 and perpendicular to the normal of the surface of the printed circuit board 6. This embodiment is suitable for the detection of vibrations that occur in the plane of the printed circuit board. For example, this embodiment is suitable for the detection of shock waves that extend along the surface of the printed circuit board 6 and parallel to the degree of freedoms of the oscillating body 5. In other words, this embodiment is suitable for horizontal mounting on a bed, where the normal of the surface of the printed circuit board 6 is parallel to the normal of the lying surface of the bed, so that shock waves parallel to the lying surface of the bed can be detected. Accordingly, the embodiment of FIG. 1 is suitable for vertical mounting on a bed, e.g. at the foot or head end of a mattress, because of the direction of the degree of freedom s of the oscillating body 5, so that shock waves parallel to the lying surface of the bed also excite an oscillation along the degree of freedom s and can thus be detected.

Figure 4:
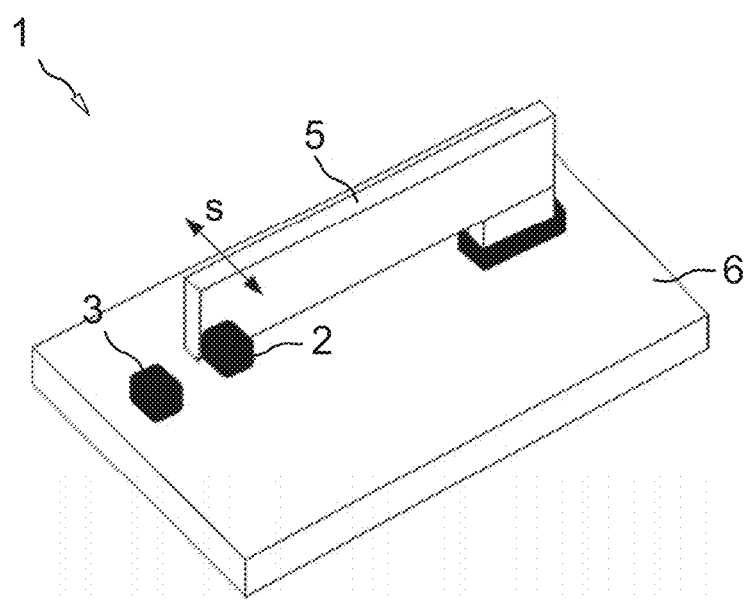

FIG. 4 shows a further embodiment of a sensor assembly 1 based on the embodiment of FIG. 3. In this embodiment, the oscillating body 5 is not part of the circuit board 6 but is a separate element, for example a flexible tab, which is connected to the circuit board, e.g. plugged on. The oscillating body 5 is, for example, a flexible or sufficiently springy printed circuit board. In this case, the oscillating body 5 can comprise the light transmitter 2 or the light receiver 3 and thus form one end of the light path 4. In contrast to FIG. 3, the oscillating body 5 is then not attached to one side of the circuit board 6, but is plugged onto the circuit board 6, for example.

Figure 5A:
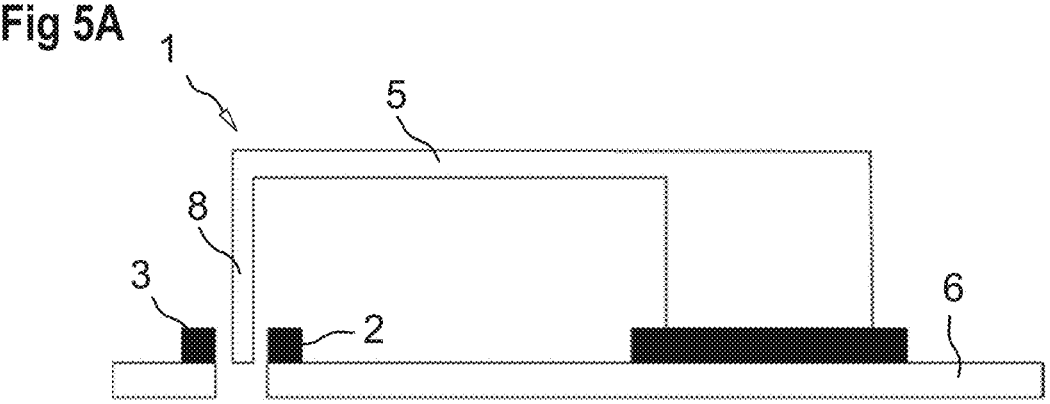
Figure 5B:
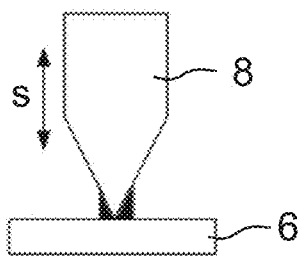

FIGS. 5A and 5B show an alternative embodiment of sensor assembly 1 with an aperture element 8 in a side or front view. The aperture element 8 is designed as part of the oscillating body 5 in the form of a tab which projects into the light path 4 between the light transmitter 2 and the light receiver 3. The oscillating body 5, for example, is made of a springy material such as spring steel, sheet metal or plastic, but does not include any electronic components. The degree of freedom s of the oscillating body 5 is perpendicular to the surface of the printed circuit board 6. Due to its shape within the light path 4, movement of the aperture element 8 influences the amount of light received by the light receiver 3. For example, the shape of the aperture element 8 is triangular in cross-section in the area of the light path. A hole in the circuit board 6 may be necessary for the vertical movement of the oscillating body 5. Instead of an aperture element 8, the oscillating body 5 can also include a translucent part 7, e.g. a lens.

Figure 6A:
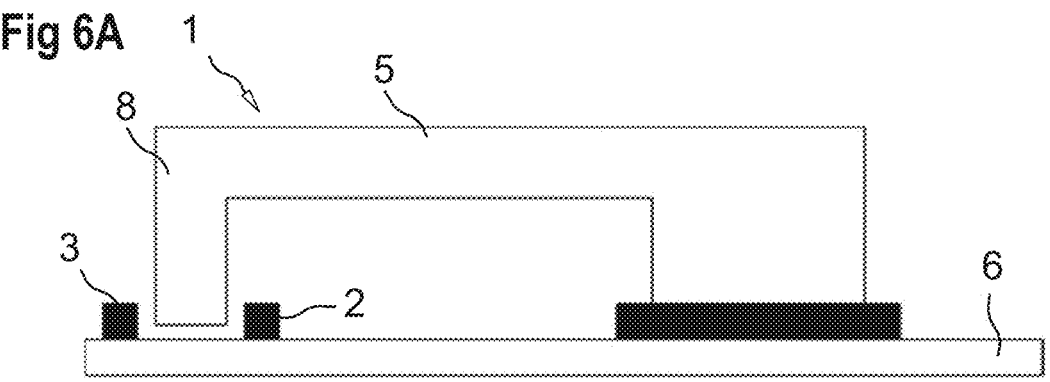
Figure 6B:
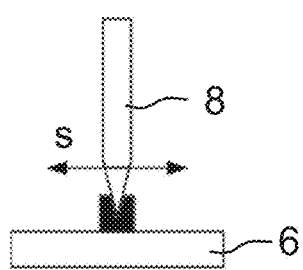

FIGS. 6A and 6B show an embodiment of the sensor assembly similar to that shown in FIGS. 5A and 5B. Here the degree of freedoms of the oscillating body 5 is parallel to the surface of the printed circuit board 6.

Figure 7:
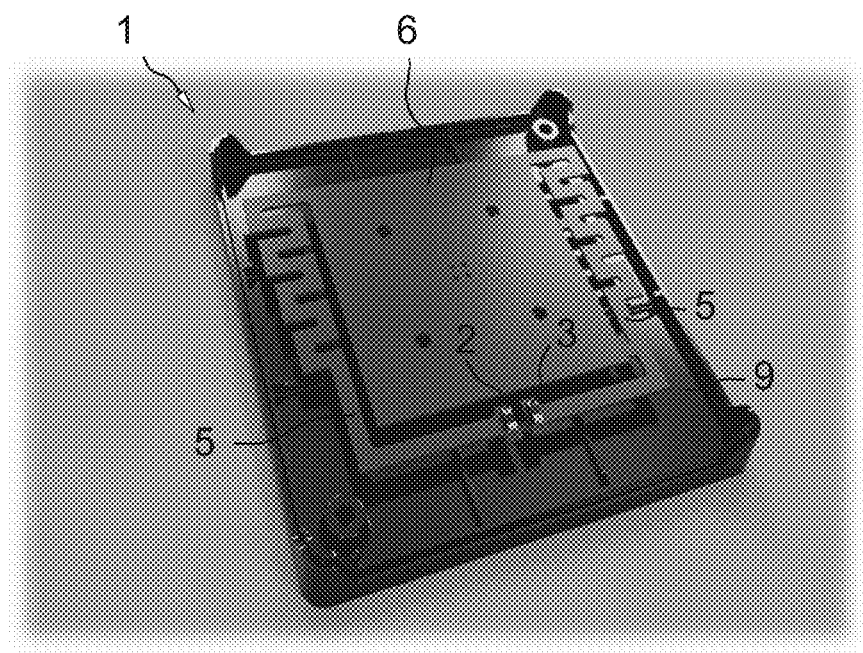

FIG. 7 shows another embodiment of a sensor assembly 1, which has two oscillating bodies 5, to which the light transmitter 2 and the light receiver 3 are attached. The oscillating bodies 5 comprise a meander-shaped suspension, via which a mechanical vibration of the two vibrating bodies 5 can occur. According to the embodiments of FIGS. 1 and 2, the degrees of freedoms of the two oscillating bodies 5 are parallel to the normal of the surface of the printed circuit board 6. Two oscillating bodies 5 can increase the sensitivity of sensor assembly 1, since the relative movement between the light transmitter 2 and the light receiver 3 can be increased. Also shown is a part of an opaque housing 9, which both allows the sensor assembly 1 to be attached to a furniture and ensures that the sensor assembly 1 or the light transmitter 2, the light receiver 3 and the oscillating body 5 are shielded from ambient light.

Figure 8:
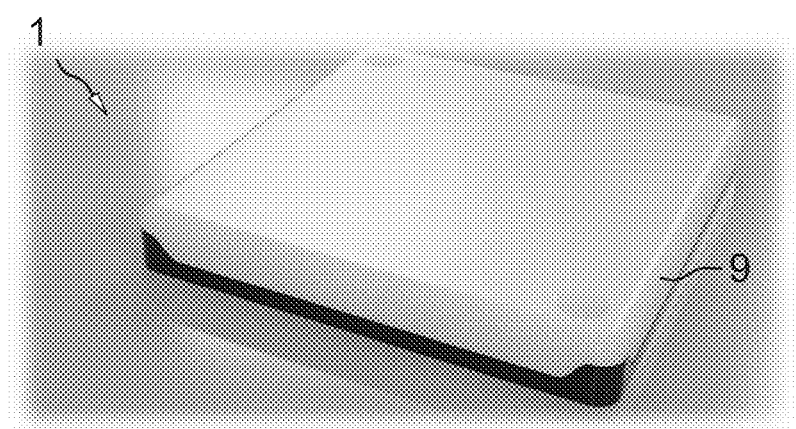
FIG. 8 shows a further example of a sensor assembly design.

FIG. 8 shows analogously the complete housing 9 of an embodiment of a sensor assembly 1, e.g. the housing 9 in this embodiment contains a sensor assembly 1 corresponding to the one shown in FIG. 3, so that this embodiment is suitable to be placed underneath a mattress of a bed and is designed to detect shock waves in horizontal direction, i.e. parallel to the lying surface.

Figure 9:
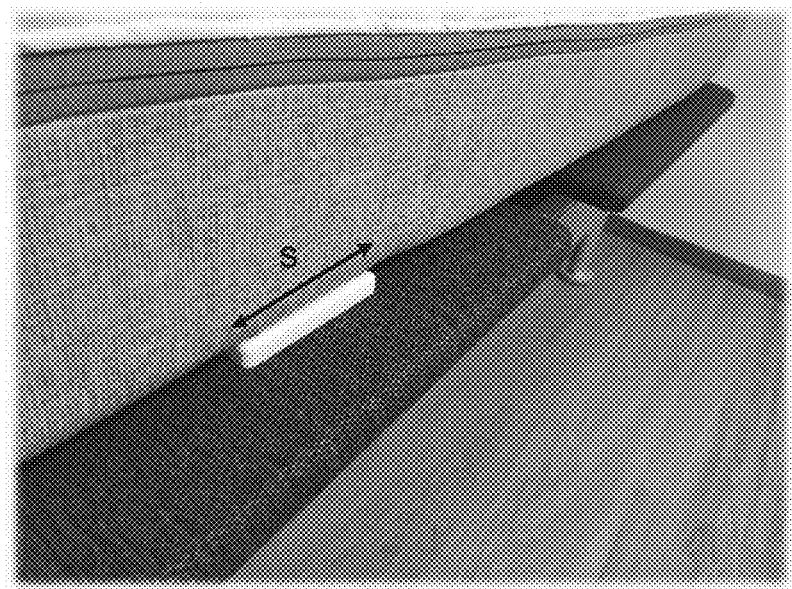
FIG. 9 shows an embodiment of a furniture system comprising a sensor assembly according to the improved measurement concept.

FIG. 9 shows a corresponding embodiment of a furniture system 10, which in this case is a bed. The sensor assembly 1 is placed under the mattress 11, as described in FIG. 8, and comprises an oscillating body 5 whose degree of freedoms is oriented parallel to the long side of the bed. This allows the oscillating body 5 to be sensitive to the heartbeat of a user lying on the mattress 11. The heartbeat causes blood to be pumped along: the blood vessels, which mainly extend towards the head or feet of the human body. For this reason, a degree of freedom s of the oscillating body 5 in the longitudinal direction of the bed or the user is a suitable choice. In addition, influences from activities that do not occur along this axis are suppressed or attenuated.

Figure 10:
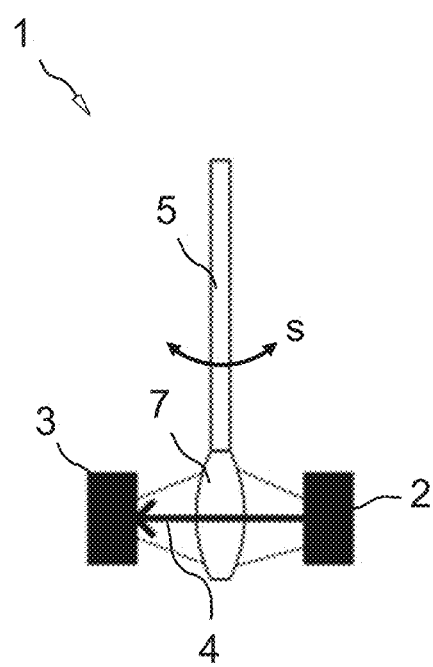
FIGS. 10 and 11 show further embodiments of a sensor assembly design.
Figure 11:
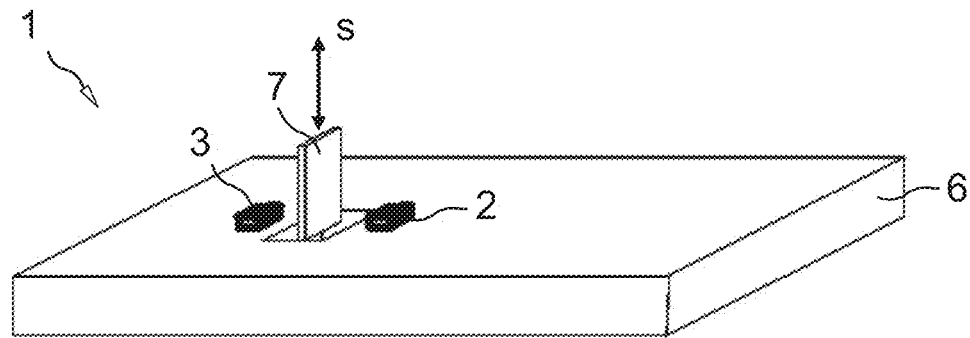

FIGS. 10 and 11 show a further embodiment of a sensor assembly 1, in which the oscillating body 5 has a translucent part 7, which is, for example, a silicate or a plastic and projects into the light path 4. Furthermore, in this embodiment, both the light transmitter 2 and the light receiver 3 are rigidly mounted relative to the oscillating body. In some embodiments, the printed circuit board 6 has an opening under the light path 4 through which the translucent part 7 can be passed. As shown schematically, the translucent part 7 moves parallel to the light path 4 or to the surface of the PCB 6 in the embodiment shown in FIG. 10 and perpendicular to the light path 4 or the surface of the PCB 6 in the embodiment shown in FIG. 11. If necessary, deviations in the range of 5° to 10° may also be possible. Thus the light path 4 or the parallel circuit board 6 forms a kind of reference line to which the oscillation refers.

The second amount of light received by the light receiver 3 depends here on the position of the translucent part 7 relative to the light path 4, i.e. the translucent part 7 causes an absorption, reflection or scattering of the incident light with a degree that depends on the deflection. For example, a thickness, an optical density or a surface roughness of the translucent part 7 varies along the degree of freedom s. Alternatively, as shown in FIG. 10, the translucent part is a lens such as a converging lens, which focuses the light onto the light receiver 3 depending on the position within the light path 4. In these designs, the standard amount of light does not necessarily correspond to the first amount of light, as there may be a limited transmissivity of the translucent part 7 in the zero deflection position.

Figure 12A:
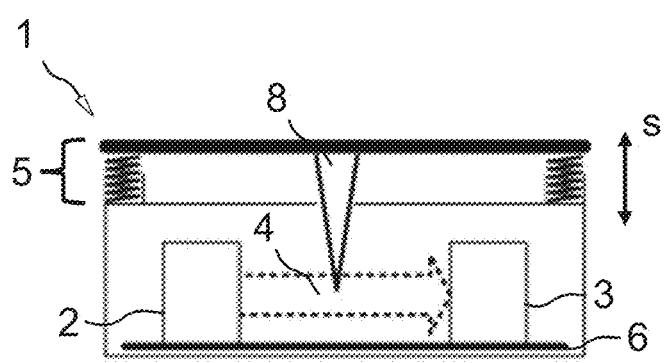
FIGS. 12A to 12C show different representations of a further embodiment of a sensor assembly according to the improved measurement concept.
Figure 12B:
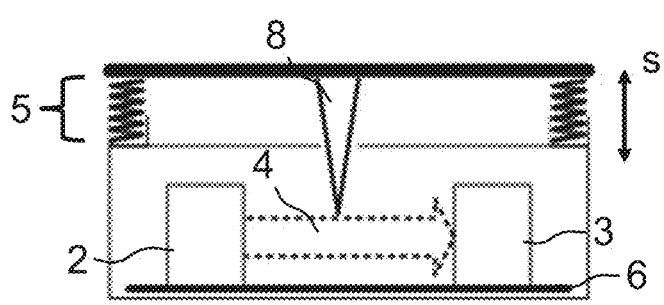
Figure 12C:
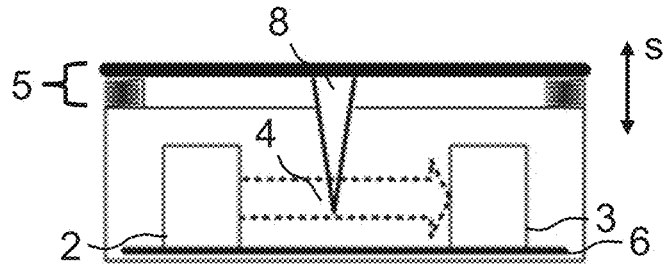

FIGS. 12A, 12B and 12C show an alternative embodiment of sensor assembly 1 with an aperture element 8 in different deflections of the oscillating body 5. The aperture element 8 is attached to the oscillating body 5. In FIGS. 12A, 12B and 12C the flexible mounting is shown by means of a spring element, but instead of a spiral spring, other flexible bodies can also be used. Similar to the embodiment of FIG. 11, the sensor assembly 1 comprises a printed circuit board 6, on which a light transmitter 2 and a light receiver 3 are located, which are optically connected to each other via a light path 4. The aperture element 8 projects into the light path 4.

While FIG. 12A shows the sensor assembly 1 in a resting state, i.e. zero deflection of the oscillating body 5, FIG. 12B shows a deflection of the oscillating body 5 away from the circuit board 6, so that the aperture element 8 projects less far into the light path 4. Conversely, in the illustration in FIG. 12C, the deflection of the oscillating body 5 is in the direction of the circuit board 6, so that the aperture element 8 projects further into the light path 4.

The arrangement shown results in the aperture element 8 allowing more or less light to pass between light transmitter 2 and the light receiver 3 via light path 4, depending on the deflection. If, with a constant emitted first amount of light, the momentary second amount of light incident on the light receiver 3 is measured, a relative measure of the momentary coverage of the light path 4 by the aperture element 8 can be determined. From the periodic change of this coverage, in turn, an oscillation frequency of the oscillating body 5 can be determined, which corresponds to a frequency of the user's activity.

The shape of the aperture element 8 can be selected in different ways. For example, aperture element 8 has the shape of a cone, a truncated cone, a pyramid, a truncated pyramid, a cylinder, a parallelepiped, a truncated cone or a shape composed of several of those shapes.

Depending on the shape of the aperture element 8, a cross-section or cross-sectional area of the aperture element 8 is obtained, which is perpendicular to the light path 4. Partial shapes are for example a segment of a circle or an ellipse segment. For example, the cross-sectional area is formed by combining a rectangle with a semicircle shape, without excluding other possible combinations.

Figure 13A:
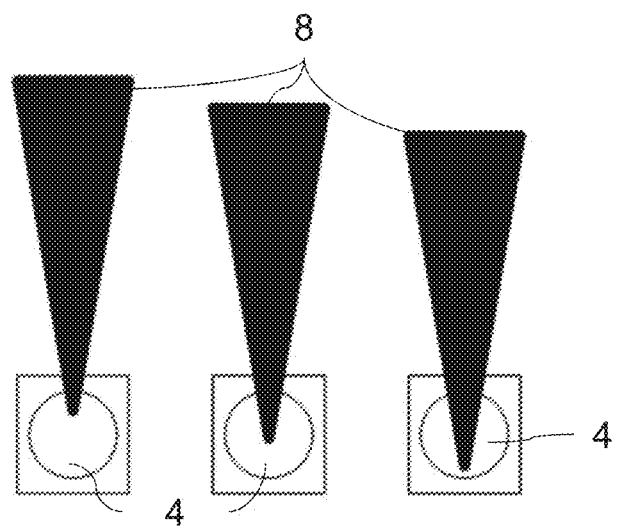
FIGS. 13A and 13B show examples of an aperture element of an embodiment of a sensor assembly.
Figure 13B:
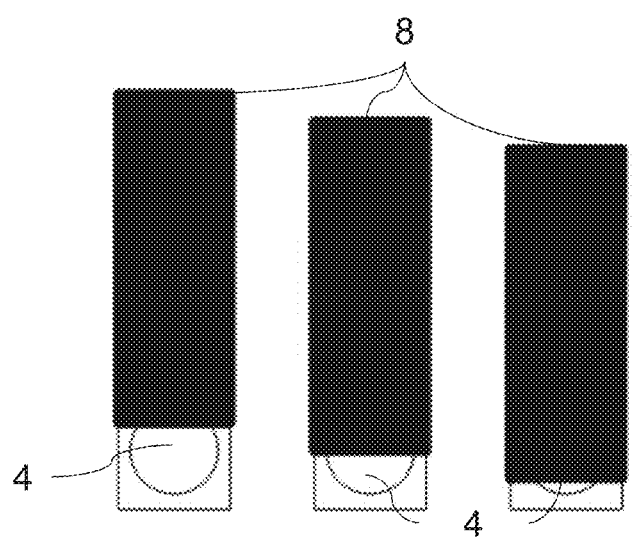

FIGS. 13A and 13B each show views of the light path 4 in plan view together with a cross-sectional area of an aperture element 8, with three different degrees of coverage shown in each case.

In FIG. 13A, the cross-sectional area of the aperture element 8 has a triangular or trapezoidal shape so that when the aperture element 8 is moved into the light path 4, the light path 4 is not suddenly interrupted. Rather, the amount of light received changes continuously as the cone of the aperture element 8 is moved further into the light path 4. This means that manufacturing tolerances of the aperture element 8 or the position of the light path 4 in relation to the aperture element 8 are less critical.

In the illustration in FIG. 13B, the aperture element 8 has a rectangular cross-sectional area which, depending on the degree of coverage of light path 4, can lead to a rather sudden interruption of light path 4. In addition, small movements of aperture element 8 can lead to relatively large changes in the received second amount of light. This can mean that manufacturing tolerances have to be observed very precisely in order to avoid a too sensitive reaction. However, such an implementation is not excluded.

Regardless of the shape of the cross-sectional area, the position of the aperture element 8 in the light path 4, for example, is selected so that without the application of force, i.e. in a resting state, the first amount of light emitted is greater by a predefined factor than the amount of light received, for example approximately twice as much. With reference to FIG. 13A and FIG. 13B, this corresponds, for example, to the respective center illustration.

Figure 14:
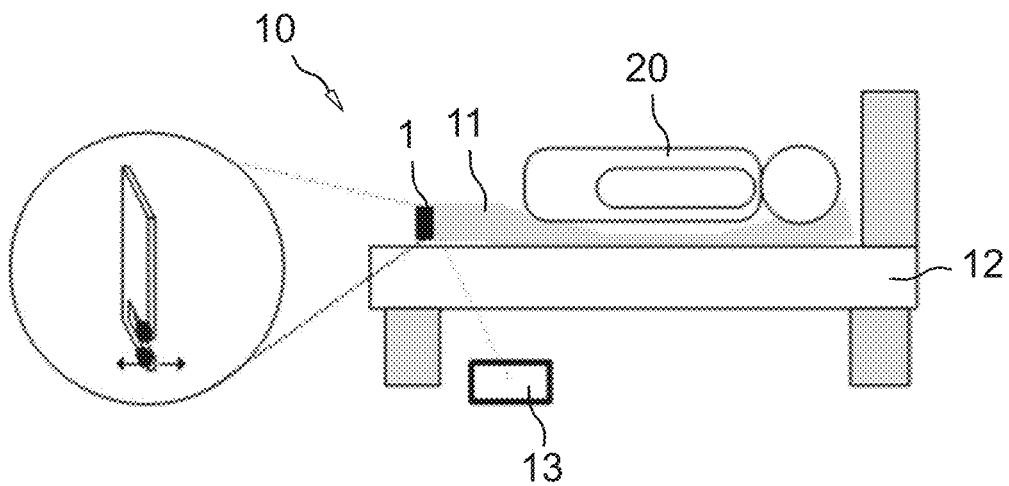
FIGS. 14 to 16 show further embodiments of a furniture comprising a sensor assembly in the form of a bed.

FIG. 14 shows an exemplary embodiment of a furniture system 10, which in this case is a bed. The sensor assembly 1 corresponds here, for example, to the embodiment of FIG. 1 and is mounted vertically at the foot end of the mattress 11 in such a way that the degree of freedom s of the oscillating body 5 is parallel to the long side of the bed or to the long side of a user 20 lying in bed. Consequently, the embodiments of sensor assembly 1, which are shown in FIGS. 2, 4, 7 and 8A to 8C, are also suitable for this purpose with the corresponding vertical alignment of the printed circuit board 6 relative to the lying surface of the mattress 11 or the longitudinal alignment of the user 20. In this embodiment, a control unit 13 contains the evaluation circuit or part of the evaluation circuit of sensor assembly 1 and is arranged in a separate housing.

Figure 15:
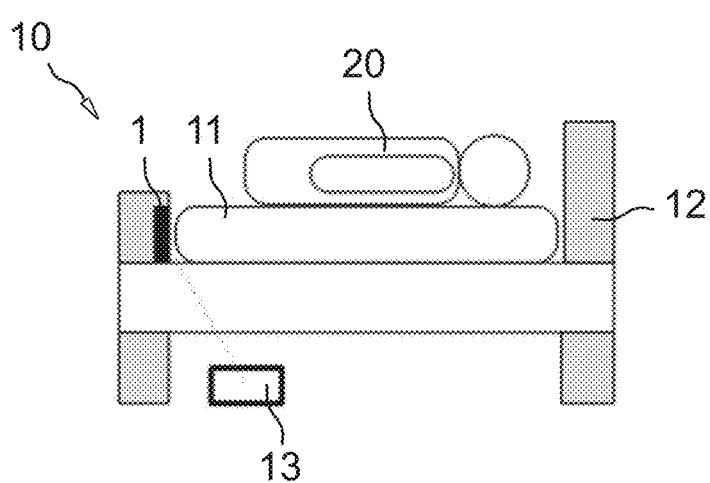

Similar to the example shown in FIG. 14, a corresponding sensor assembly 1 as shown in FIG. 15 can alternatively be located on or in a part of the frame 12 of the bed. In particular, the sensor assembly 1 can be located in a cavity of the frame 12, so that the sensor assembly 1 is protected from ambient light even without its own housing 9.

Figure 16:
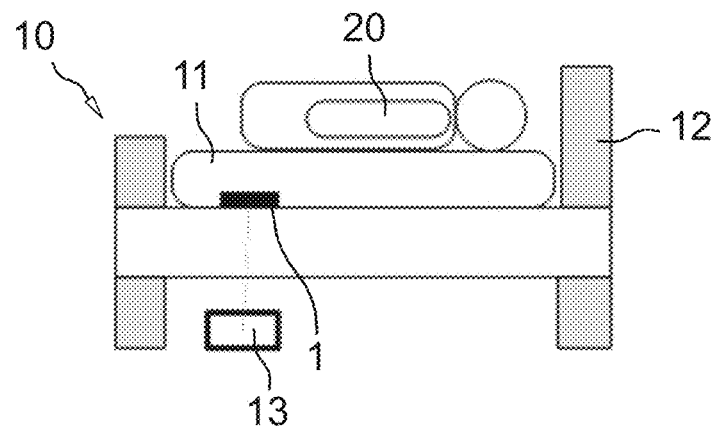

FIG. 16 shows an exemplary embodiment of a furniture system 10 according to the example shown in FIG. 9. Here the sensor assembly 1 is arranged horizontally under the mattress 11, so that the surface of the printed circuit board. 6 is parallel to the lying surface of the mattress 11. In order for the degree of freedom s of the oscillating body 5 also being parallel to the long side of the bed, an embodiment of the sensor assembly according to the embodiment of FIG. 3 is suitable here, in which the degree of freedom s is parallel to the surface of the printed circuit board 6.

The use of the sensor assembly 1 in other adjustable furniture, such as tables and seating furniture, is not excluded. For example, a presence detection can be carried out that provides information on how long a user has been lying or sitting or how long he has been working at a table.

The invention claimed is:

1. A sensor assembly for a furniture for detecting an activity of a user of the furniture, the sensor assembly comprising:
   a light transmitter and a light receiver forming beginning and end of an optical light path connecting the light transmitter and the light receiver, wherein the light receiver is adapted to output a reception signal based on a received amount of light;
   an evaluation circuit configured to generate a motion signal based on the reception signal or a signal derived from the reception signal; and
   an oscillating body which is movably mounted in such a manner that a movement of the oscillating body results in a change in a property of the light path;

wherein the sensor assembly is arranged such that the activity of the user is to cause the oscillating body to oscillate, and wherein the oscillating body has a resonant frequency of less than 20 Hz.

2. The sensor assembly according to claim 1, wherein the oscillation influences the amount of light received by the light receiver from the light transmitter.

3. The sensor assembly according to claim 1, wherein the evaluation circuit is further configured
- to control an amount of light emitted by the light transmitter by means of a control signal resulting from minimizing a difference between the reception signal and a reference signal; and
- to generate the motion signal based on the control signal or on a signal derived from the control signal.

4. The sensor assembly according to claim 1, wherein the activity is a biological activity and comprises at least one of the following:
- heartbeat;
- pulse;
- movement;
- sounds;
- breathing.

5. The sensor assembly according to claim 1, wherein the oscillating body is movably arranged in such a manner that the oscillating body has only one mechanical degree of freedom.

6. The sensor assembly according to claim 1, wherein the oscillating body has the resonant frequency in the range of 12-14 Hz.

7. The sensor assembly according to claim 1, wherein the light path is realized as a direct optical connection for transmitting light from the light transmitter to the light receiver, in particular without a use of reflections.

8. The sensor assembly according to claim 1, wherein the light path is shorter than 1 cm, in particular shorter than 5 mm.

9. The sensor assembly according to claim 1, wherein the light transmitter or the light receiver is attached to the oscillating body.

10. The sensor assembly according to claim 9, further comprising a printed circuit board on which at least a part of the evaluation circuit is arranged, wherein the oscillating body is a part of the printed circuit board or is connected to the printed circuit board.

11. The sensor assembly according to claim 1, wherein the oscillating body is arranged between the light transmitter and the light receiver in such a manner that a translucent part of the oscillating body is located on the light path, wherein the movement of the oscillating body causes a change in an optical property of the light path within the translucent part.

12. The sensor assembly according to claim 11, wherein the translucent part is characterized by a transmission which is dependent on a position and/or an extension direction of the optical light path within the translucent part.

13. The sensor assembly according to claim 1, wherein the oscillating body comprises an aperture element which is configured to at least partially cover the light path, wherein the movement of the oscillating body causes a change in coverage of the light path.

14. The sensor assembly according to claim 1, further comprising a printed circuit board on which at least part of the evaluation circuit is arranged.

15. The sensor assembly according to claim 14, wherein the light path extends parallel to a main extension plane of the printed circuit board.

16. The sensor assembly according to claim 14, wherein the oscillating body is movably arranged in such a manner that the oscillation is either parallel or perpendicular to a main plane of extension of the printed circuit board.

17. The sensor assembly according to claim 1, further comprising a housing, in particular a light-protected housing, in which the light transmitter, the light receiver and the oscillating body are arranged.

18. The sensor assembly according to claim 1, further comprising additional light transmitters and/or light receivers, wherein each light receiver is connected to at least one light transmitter via an optical light path.

19. A furniture comprising a furniture frame and a sensor assembly according to claim 1, wherein the sensor assembly is attached to the furniture frame in such a way that the light transmitter, the light receiver and the oscillating body are isolated from an ambient light.

20. The furniture according to claim 19, wherein the sensor assembly is arranged in a cavity, in particular in a light-protected cavity of the furniture frame.

21. The furniture according to claim 19, wherein the furniture is one of the following:
- a table;
- a seating unit;
- a bed.

22. The furniture according to claim 19, wherein
the furniture is a bed; and
the oscillating body of the sensor assembly is aligned in such a way that a deflection of the oscillation is parallel to a longitudinal direction of the bed.

23. The furniture according to claim 19, wherein the sensor assembly is configured to perform a presence detection.

24. The furniture according to claim 19, wherein at least one component of the furniture is adjustable, in particular electrically adjustable by means of an actuator and a control of the furniture.

25. A method for detecting an activity of a user of a furniture with at least one sensor assembly, the at least one sensor assembly comprising a light transmitter and a light receiver, which form beginning and end of an optical light path, which connects the light transmitter and the light receiver to one another, and an oscillating body, which is arranged movably in such a way that a movement of the oscillating body results in a change in a property of the light path, the method comprising:
- transmitting a first amount of light from the light transmitter via the light path to the light receiver;
- generating, with the light receiver, a reception signal based on a second amount of light received via the light path;
- converting the activity of the user into a change in the movement of the oscillating body relative to the light path;
- generating a motion signal based on at least the second amount of light or on a signal derived from the second amount of light; and
- recognizing, based on the motion signal, in particular based on a change in the motion signal, the activity of the user,
wherein the oscillating body has a resonant frequency of less than 20 Hz.

* * * * *